United States Patent
Schönfelder et al.

(10) Patent No.: US 10,980,903 B2
(45) Date of Patent: Apr. 20, 2021

(54) METHOD FOR IRRADIATING A LIQUID WITH ACCELERATED ELECTRONS

(71) Applicant: Fraunhofer-Gesellschaft zur Förderung der angewandten Forschung e.V., Munich (DE)

(72) Inventors: Jessy Schönfelder, Dresden (DE); Frank-Holm Rögner, Dresden (DE); Javier Portillo Casado, Dresden (DE); Jörg Kubusch, Dresden (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 16/308,200

(22) PCT Filed: Jun. 8, 2017

(86) PCT No.: PCT/EP2017/064034
§ 371 (c)(1),
(2) Date: Dec. 7, 2018

(87) PCT Pub. No.: WO2017/211990
PCT Pub. Date: Dec. 14, 2017

(65) Prior Publication Data
US 2019/0175769 A1 Jun. 13, 2019

(30) Foreign Application Priority Data
Jun. 9, 2016 (DE) ..................... 10 2016 110 672.0

(51) Int. Cl.
*A61L 2/00* (2006.01)
*A61L 2/08* (2006.01)
(Continued)

(52) U.S. Cl.
CPC .............. *A61L 2/007* (2013.01); *A61L 2/087* (2013.01); *A61L 2/10* (2013.01); *C02F 1/305* (2013.01);
(Continued)

(58) Field of Classification Search
CPC . A61L 2/007; A61L 2/10; A61L 2/087; A61L 2202/21; C02F 1/32; C02F 1/305; C02F 2303/04
See application file for complete search history.

(56) References Cited

U.S. PATENT DOCUMENTS 3,988,588 A  10/1976  Offermann
4,230,947 A  10/1980  Cram
(Continued)

FOREIGN PATENT DOCUMENTS

CN  1428604 A  7/2003
CN  203169652 U  9/2013
(Continued)

OTHER PUBLICATIONS

UV treatment of Orange Juice (Year: 2004).*
(Continued)

*Primary Examiner* — Sean E Conley
*Assistant Examiner* — Brendan A Hensel
(74) *Attorney, Agent, or Firm* — Brinks Gilson & Lione

(57) ABSTRACT

Methods and Apparatus are provided for irradiating a liquid with accelerated electrons. The liquid is prepared. The liquid is mixed with particles having at least one luminescent substance, where the particles are formed such that the particles are dispersed in the liquid after mixing. The liquid is irradiated with an electromagnetic radiation, which induces the at least one luminescent substance to luminesce. An actual value of a physical quantity characterizing the luminescence of the luminescent substance is detected. The
(Continued)

liquid is irradiated with accelerated electrons until the detected actual value corresponds to a target value.

10 Claims, 2 Drawing Sheets

(51) Int. Cl.
    *A61L 2/10*     (2006.01)
    *C02F 1/30*     (2006.01)
    *C02F 1/32*     (2006.01)

(52) U.S. Cl.
    CPC .............. *C02F 1/32* (2013.01); *A61L 2202/21* (2013.01); *C02F 2303/04* (2013.01)

(56) References Cited

U.S. PATENT DOCUMENTS

| | | | | |
|---|---|---|---|---|
| 4,775,598 A | * | 10/1988 | Jaeckel | B22F 1/0051 419/19 |
| 5,962,857 A | * | 10/1999 | McKeever | G01T 1/105 250/484.5 |
| 2009/0294692 A1 | * | 12/2009 | Bourke, Jr. | A23L 2/50 250/459.1 |
| 2014/0369885 A1 | * | 12/2014 | Krueger | A61L 2/087 422/22 |
| 2017/0072082 A1 | * | 3/2017 | Jurak | A61L 2/10 |

FOREIGN PATENT DOCUMENTS

| | | |
|---|---|---|
| DE | 10 2013 109390 A1 | 3/2015 |
| DE | 10 2015 117939 A1 | 4/2017 |

OTHER PUBLICATIONS

Plank-Einstein relation (Year: 0).*
English translation of International Search Report, issued in International Application No. PCT/EP2017/064034, dated Sep. 4, 2017, pp. 1-2, European Patent Office, Rijswijk, Netherlands.
Chinese First Office Action with English translation, issued in CN Application 201780035515.7, dated Jun. 8, 2020, pp. 1-23, National Intellectual Property Administration, Beijing, P.R. China.

* cited by examiner

METHOD FOR IRRADIATING A LIQUID WITH ACCELERATED ELECTRONS

CROSS-REFERENCE TO RELATED APPLICATIONS

This application is a 371 nationalization of international patent application PCT/EP2017/064034 filed Jun. 8, 2017, which claims priority under 35 USC § 119 to German patent application DE 10 2016 110 672.0, filed Jun. 9, 2016. The entire contents of each of the above-identified applications are hereby incorporated by reference.

TECHNICAL FIELD

The invention relates to a method for irradiating a liquid with accelerated electrons, wherein the dose of the energy input into the liquid can be monitored and/or adjusted.

DETAILED DESCRIPTION

Figure 1:
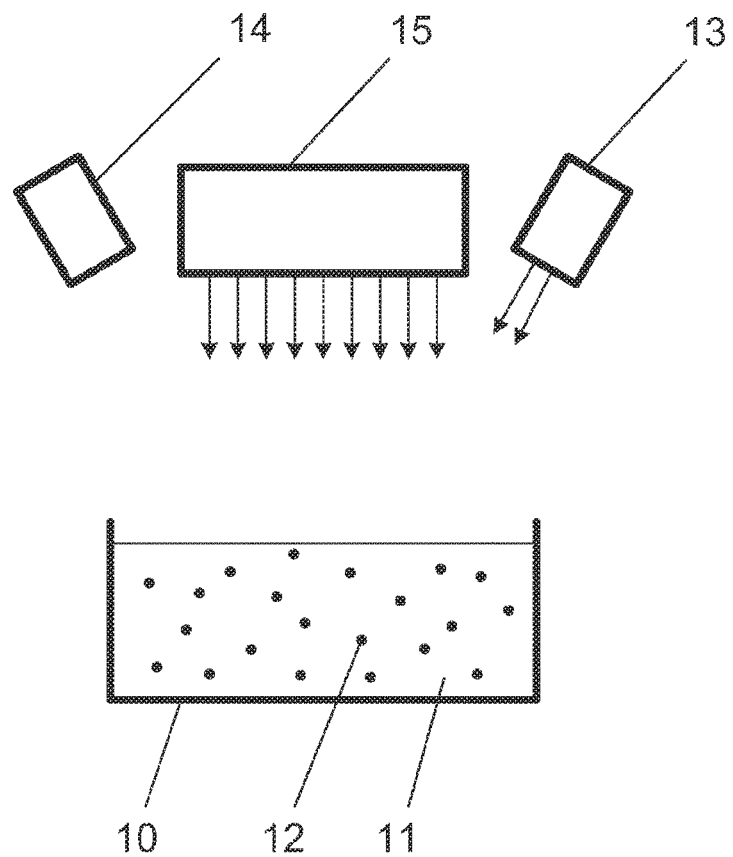
FIG. 1 a schematic view of a configuration for performing the inventive method.

Various methods are known in which liquids are irradiated with accelerated electrons in order to inactivate dangerous microorganisms in the liquids. In U.S. Pat. No. 4,230,947 A, a liquid is lifted onto a plateau on the basis of the liquid level in a feeding tube system, from which plateau it then falls down as a liquid curtain. During the free fall, this curtain is irradiated with accelerated electrons. U.S. Pat. No. 3,988,588 A discloses methods in which a funnel-shaped device is used, whereby a stratified volume of a liquid is formed through overflow or rotation, and this volume is then irradiated with accelerated electrons. In both methods, however, it is not possible to monitor or adjust the energy dose input into the liquid.

DE 10 2013 109 390 A1 describes a method in which a packaging material for liquid or solid material is sterilized. Here, a marker material field is applied to the packaging material, which comprises at least one inorganic luminescent substance. The marker material field is radiated with electrons, whereby the luminescence lifetime of the luminescent substance is changed. Using the change of the luminescence lifetime of the luminescent substance, it can be determined whether the marker material field has been sufficiently radiated with electrons. In this method, the energy dose that has been input into the marker material field can be precisely determined and adjusted. However, it can only be approximately determined which energy dose has actually been applied in the solid or liquid materials that are encased in the packaging material.

The invention is therefore based upon the technical problem of creating a method for the irradiation of a liquid with accelerated electrons, whereby the disadvantages of the prior art can be overcome.

In particular, it should be possible with the inventive method to monitor and/or adjust the dose during the irradiation of a liquid with accelerated electrons.

In the inventive method, a liquid to be irradiated with accelerated electrons is first prepared. Particles having at least one luminescent substance are mixed with this liquid, wherein the particles are formed such that the particles are dispersed in the liquid after mixing. Within the meaning of the invention, particles are dispersed within a liquid when their sinking and rising velocity within a non-flowing volume of the liquid is less than 100 nm/s. Subsequently, the liquid mixed with the particles is irradiated with an electromagnetic radiation, which induces the at least one luminescent substance to luminescence. Such an electromagnetic radiation can be, for example, light that is detectable by the human eye or also UV radiation. During and/or directly after irradiating the liquid with the electromagnetic radiation, an actual value for at least one physical quantity characterizing the luminescence of the luminescent substance is detected via a detector and transmitted to an evaluation device. A physical quantity characterizing the luminescence of the luminescent substance can be, for example, the luminescence lifetime, the intensity of at least one wavelength of the luminescence, or the wavelength at which the luminescence reaches its maximum intensity. Further, in the inventive method, the liquid mixed with particles, and thus also the luminescent substance of the particles mixed with the liquid, are irradiated with accelerated electrons. Through the irradiation of a luminescent substance with accelerated electrons, parameters of physical quantities that characterize the luminescence of the luminescent substance are changed. Therefore, according to the invention, the liquid mixed with particles is irradiated with accelerated particles until the actual value of the at least one quantity characterizing the fluorescence of the luminescent substance, detected continuously or at intervals by the detector, corresponds to a target value. In this way, the dose at which a liquid is to be irradiated with accelerated electrons can be monitored and adjusted.

Figure 2:
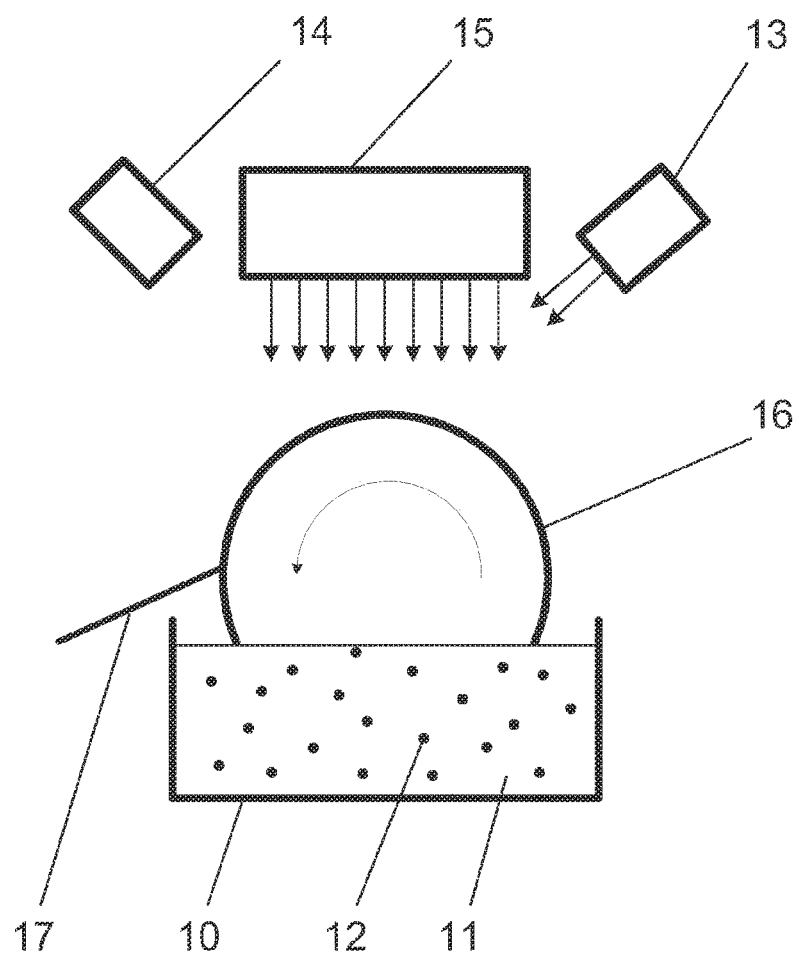
FIG. 2 a schematic view of an alternative configuration for performing the inventive method.

The present invention is explained in greater detail below with reference to exemplary embodiments. The figures show:

FIG. 1 a schematic view of a configuration for performing the inventive method;

FIG. 2 a schematic view of an alternative configuration for performing the inventive method.

An apparatus schematically shown in FIG. 1, which is for carrying out the inventive method, comprises a vessel 10 in which a liquid 11, for example a vaccine, is prepared. The vessel 10 consists of an inflexible material. Alternatively, the liquid 11 can also be in a container made of a flexible material during the performance of the inventive method. Such a container can therefore be, for example, a foil bag.

The liquid 11 in the form of a vaccine is interspersed with microorganisms, for example viruses, which are to be inactivated by irradiating with accelerated electrons. For the inactivation of the vaccine, a certain dose is required, which may not be too low, in order to inactivate as many of the microorganisms in the vaccine as possible. Here, the dose is the energy quantity that is absorbed during the irradiating with accelerated electrons per unit of mass of the liquid 11. However, the dose may also not be too high, because this could have a negative impact on the effectiveness of the vaccine. The optimal dose for a given case is determined in laboratory trials.

According to the invention, the liquid is mixed with particles 12 containing at least one luminescent substance before irradiating with accelerated electrons. The particles 12 used for the inventive method can consist completely of the luminescent substance or, alternatively, of a base material upon whose surface the luminescent substance is applied and/or in which the luminescent substance is embedded. In one embodiment, the particles consist of a biocompatible material. This is especially advantageous if the inventive method is performed on vaccines, as described in the exemplary embodiment. In a further embodiment, the base material fully encases the at least one luminescent substance.

All luminescent substances known from the prior art that can be induced to luminesce by way of the irradiation with an electromagnetic radiation are suitable as the luminescent substance for the inventive method. The at least one luminescent substance can be, for example: a cyanate, rhodamine or a derivative thereof, an oxide, an oxyhalide, a sulfide, an oxysulfide, a sulfate, an oxysulfate, a selenide, a nitride, an oxynitride, a nitrate, an oxynitrate, a phosphide, a phosphate, a carbonate, a silicate, an oxysilicate, a vanadate, a molybdate, a tungstate, a germanate, an oxygermanate, or a halide of the elements Li, Na, K, Rb, Mg, Ca, Sr, Sc, Y, La, Ti, Zr, Hf, Nb, Ta, Zn, Gd, Lu, Al, Ga and/or In. Preferably, the luminescent substance or at least one of the luminescent substances contain one or more ions of the group In+, $Sn^{2+}$, $Pb^{2+}$, $Sb^{3+}$, $Bi^{3+}$, $Ce^{3+}$, $Ce^{4+}$, $Pr^{3+}$, $Nd^{3+}$, $Sm^{2+}$, $Sm^{3+}$, $Eu^{2+}$, $Eu^{3+}$, $Gd^{3+}$, $Tb^{3+}$, $Dy^{3+}$, $Ho^{3+}$, $Er^{3+}$, $Tm^{2+}$, $Tm^{3+}$, $Yb^{2+}$, $Yb^{3+}$, $Ti^{3+}$, $V^{2+}$, $V^{3+}$, $V^{4+}$, $Cr^{3+}$, $Mn^{2+}$, $Mn^{3+}$, $Mn^{4+}$, $Fe^{3+}$, $Fe^{4+}$, $Fe^{5+}$, $Co^{3+}$, $Co^{4+}$, $Ni^{2+}$, $Cu^+$, $Ru^{2+}$, $Ru^{3+}$, $Pd^{2+}$, $Ag^+$, $Ir^{3+}$, $Pt^{2+}$ and $Au^+$.

For the inventive method, the particles 12 are formed such that they are dispersed in the liquid 11 after mixing with the liquid 11. This can essentially be adjusted by way of two parameters, the size and/or density of the particles 12. In one embodiment of the inventive method, the particles 12 are formed with a size in the nanometer or micrometer range. It is also advantageous if the particles 12 have a density that corresponds to the density of the liquid 11. If the particles 12 have another base material in addition to the luminescent substance, plastics can also be used as the base material, because plastics with a density similar to the density of liquids can be manufactured. In the exemplary embodiment described in FIG. 1, the particles 12 consist of a base material formed as a plastic, upon whose surface a luminescent substance known under the name "FITC" is applied to half of the particles and a luminescent substance known under the name "PE" is applied to the other half of the particles.

The configuration from FIG. 1 further comprises a device 13 for the transmission of an electromagnetic radiation, whereby the liquid 11, and thus also the particles 12 dispersed therein, are irradiated and the luminescent substance contained in the particles 12 is induced to luminesce. In one embodiment, the luminescent substance is fully encased by the base material of the particles, wherein the base material is transparent vis-à-vis the electromagnetic radiation. In one embodiment, the electromagnetic radiation is emitted from the device 13 in pulse form.

During and/or directly after the irradiation of the liquid 11 with the electromagnetic radiation, an actual value for the luminescence lifetime is determined via a detector 14, transmitted to an evaluation device not shown in FIG. 1, and there compared to a target value for the luminescence lifetime.

Using an electron generator 15, accelerated electrons are produced, with which the liquid 11 and the particles 12 contained therein are irradiated, whereby the luminescence lifetime of the luminescent substance contained in the particles is changed. In the inventive method, a ribbon radiator or a planar radiator can be used as the electron generator 15.

The irradiation of the liquid 11 with accelerated electrons occurs until the actual value of the luminescence lifetime detected by the detector 14 corresponds to the target value, whereby the dose with which the liquid 11 is to be irradiated with accelerated electrons, as previously determined in laboratory trials, is achieved.

FIG. 1 shows a configuration whereby a liquid volume can be irradiated with accelerated electrons with no relative movement of the electron generator 15, the device 13, or the detector 14. FIG. 2 schematically shows an alternative configuration whereby a liquid volume can be irradiated with accelerated electrons with relative movement of the electron generator 15, the device 13, and the detector 14.

The configuration shown in FIG. 2 has all of the features of the configuration from FIG. 1. Additionally, the configuration shown in FIG. 2 comprises a cylinder 16, which partially projects into the liquid 11 and turns in a counter-clockwise direction. A fluid film is thereby created on the surface of the cylinder 16, brought within an effective range of device 13, detector 14, and electron generator 15 by way of the progressive rotation of the cylinder 16, and finally removed from the cylinder 16 by a wiper 17. In this way, the fluid film and the particles 12 contained therein are irradiated with the electromagnetic radiation of the device 13, whereby the luminescent substance of the particles 12 is induced to luminesce. The detector 14 determines an actual value for the luminescence lifetime, which is compared to a target value in an evaluation device. The fluid film on the cylinder 16 is also irradiated with accelerated electrons of the electron generator 15 until the actual value of the luminescence lifetime corresponds to the target value.

The applied dose of accelerated electrons with which a section of the fluid film on the cylinder 16 is irradiated can be adjusted in the case of a configuration according to FIG. 2, in that, for example, the rotational velocity of the cylinder 16 and/or the power of the electron generator 15 are regulated on the basis of a detected actual value of the luminescence lifetime. If the electron generator 15 is operated in a pulsed fashion, the length of the pulses and/or the length of the pulse pauses can additionally or alternatively be regulated based on a detected actual value of the luminescence lifetime.

The configurations shown in FIG. 1 and FIG. 2 are given merely as examples. Alternatively, for the performance of the inventive method, all other configurations in which a liquid volume can be irradiated with accelerated with or without a relative velocity of an electron generator are suitable.

To clarify the use of and to hereby provide notice to the public, the phrases "at least one of <A>, <B>, ... and <N>" or "at least one of <A>, <B>, <N>, or combinations thereof" or "<A>, <B>, ... and/or <N>" are defined by the Applicant in the broadest sense, superseding any other implied definitions hereinbefore or hereinafter unless expressly asserted by the Applicant to the contrary, to mean one or more elements selected from the group comprising A, B, ... and N. In other words, the phrases mean any combination of one or more of the elements A, B, ... or N including any one element alone or the one element in combination with one or more of the other elements which may also include, in combination, additional elements not listed.

Unless otherwise indicated or the context suggests otherwise, as used herein, "a" or "an" means "at least one" or "one or more."

The invention claimed is:

1. A method for irradiating a liquid with accelerated electrons, the method comprising:
preparing the liquid;
mixing the liquid with particles, which have at least one luminescent substance, wherein the particles are formed such the particles are dispersed in the liquid after mixing, wherein the particles are dispersed within the liquid when sinking and rising velocities of the particles within a non-flowing volume of the liquid are less than 100 nm/s;

detecting an actual value of a physical quantity characterizing a luminescence of the luminescent substance in the liquid by irradiating the liquid with an electromagnetic radiation, which induces the at least one luminescent substance to luminesce;

inactivating microorganisms in the liquid with a plurality of accelerated electrons by irradiating the liquid with the accelerated electrons until the actual value of the physical quantity characterizing the luminescence of the luminescent substance detected has changed from an initial value to a target value, wherein the physical quantity characterizing the luminescence of the luminescent substance is changed from the initial value to the target value by the accelerated electrons.

2. The method of claim 1, wherein UV radiation or light is used as the electromagnetic radiation.

3. The method of claim 1, wherein the particles comprise a base material upon whose surface the luminescent substance is applied and/or in which the luminescent substance is embedded.

4. The method of claim 3, wherein the base material comprises a plastic.

5. The method of claim 3, wherein the base material comprises a biocompatible material.

6. The method of claim 3, wherein the luminescent substance is embedded in the base material, and the luminescent substance is fully encased by the base material, which is transparent with respect to the electromagnetic radiation.

7. The method of claim 1, wherein the size and/or the density of the particles is selected such that the particles are dispersed in the liquid after mixing.

8. The method of claim 1, further comprising forming the liquid into a fluid film before irradiating with accelerated electrons.

9. The method of claim 1, wherein the physical quantity characterizing the luminescence of the luminescent substance comprises: luminescence lifetime, intensity of at least one wavelength of the luminescence, or a wavelength at which the luminescence reaches its maximum intensity.

10. The method of claim 1, wherein detecting the initial value and the target value of the actual value of the physical quantity characterizing the luminescence of the luminescent substance is detected while irradiating the liquid with accelerated electrons.

* * * * *

UNITED STATES PATENT AND TRADEMARK OFFICE
CERTIFICATE OF CORRECTION

Page 1 of 1

PATENT NO. : 10,980,903 B2
APPLICATION NO. : 16/308200
DATED : April 20, 2021
INVENTOR(S) : Jessy Schönfelder et al.

It is certified that error appears in the above-identified patent and that said Letters Patent is hereby corrected as shown below:

In the Claims

Column 5, Claim 1, Line 10, after the ";", insert --and--.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*